US007000852B1

(12) United States Patent
Chiu

(10) Patent No.: US 7,000,852 B1
(45) Date of Patent: Feb. 21, 2006

(54) EVAPORATIVE SCENT BURNER PROVIDED WITH A GYPSUM EVAPORATIVE BASE

(76) Inventor: Hsiu-Feng Chiu, 7F.-1, No. 337, Sec. 4, Sinyi Rd., Taipei City (TW)

( * ) Notice: Subject to any disclaimer, the term of this patent is extended or adjusted under 35 U.S.C. 154(b) by 192 days.

(21) Appl. No.: 10/771,967

(22) Filed: Feb. 5, 2004

(51) Int. Cl.
 *A61L 9/04* (2006.01)
(52) U.S. Cl. .............................. 239/44; 239/34; 239/45; 239/53; 422/123
(58) Field of Classification Search ................ 239/34, 239/42, 44, 53, 45, 57; 422/123, 125
 See application file for complete search history.

(56) References Cited

U.S. PATENT DOCUMENTS 4,915,301 A * 4/1990 Munteanu .................... 239/45
 6,555,069 B1 * 4/2003 Ferguson .................... 422/126

\* cited by examiner

Primary Examiner—John Kim
Assistant Examiner—Sean E. Conley
(74) Attorney, Agent, or Firm—Alan D. Kamrath; Nikolai & Mersereau, P.A.

(57) ABSTRACT

An evaporative scent burner comprises a bottle, which is used to accommodate the essential oil, with its top provided with a bottle mouth, a gypsum evaporative base, with its bottom provided onto the bottle mouth of above-mentioned bottle and its top designed with an enlargement surface, a braided wire, which head is connected to the gypsum evaporative base while the bottom of the braided wire will fall inside the bottle to absorb essential oil. The advantages of the present invention include: A reinforcement base, which is built-in the gypsum evaporative base and constructed of rigid materials of strong toughness. The screw notch of reinforcement base is provided with a punching hole, where braided wire can cross through and the braided wire head can be fastened. Besides, this reinforcement base is available with a ring-type wall to separate braided wire and gypsum evaporative base, so as to prevent the gypsum evaporative base from breakdown or strip for a leak-proof efficiency.

3 Claims, 7 Drawing Sheets

EVAPORATIVE SCENT BURNER PROVIDED WITH A GYPSUM EVAPORATIVE BASE

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention relates generally to an evaporative scent burner, and more particularly to an evaporative scent burner which is provided with a gypsum evaporative base for reinforcement.

BACKGROUND OF THE INVENTION

Coupling with an improved living standard and taste of life in modern era, an evaporative scent burner is widely applicable in a gradual manner. Now, this industry has developed several types of evaporative scent burners. The common features of existing evaporative scent burners include: firstly, the braided wire head shall be ignited for warming-up, then extinguish the fire and enable the essential oil to evaporate via residual heat. Additionally, this industry has also developed an electric evaporative scent burner. However, as ignition mode is concerned, there are recently found some explosion accidents owing to improper utilization of end-users, which led to sharply reduced willingness and confidence of purchase. And, electric evaporative scent burner will waste electricity in despite of higher safety, thus increasing its cost to the dissatisfaction of end-users. Thereupon, this industry has developed a volatile evaporative scent burner as shown in FIG. 6. The feature of this burner is that a gypsum evaporative base 52 is provided at bottle mouth 51 of evaporative scent burner. A screw hole 53 is provided at the gypsum evaporative base so as to screw it at the bottle mouth 51 while a braided wire 54 is placed inside the screw hole 53 for top connection. The bottom of the braided wire 54 shall fall inside the bottle 50 to absorb essential oil 55. Therefore, evaporation of essential oil is possible owing to the capillary porosity of gypsum evaporative base 52. However, this structure has the following problems to be addressed.

Constructed of fragile gypsum, the ring-type slot wall of screw hole 53 at the gypsum evaporative base 52 cannot withstand the twisting force at the bottle mouth 51 applied by the end-users. Therefore, helical tooth will break down or even break off after the end-users have dismantled the gypsum evaporative base 52 several times as shown in FIG. 7. In such case, there is a possibility of strip when the gypsum evaporative base 52 is fastened at the bottle mouth 51. And, in the event of the damage of helical tooth, the essential oil 55 inside the bottle 50 is prone to leakage. Additionally, breakdown is also possible when the braided wire has attrited the corner 56 of screw hole 53. Thus, this industry shall make efforts to address it for the sake of the customers.

Based upon the aforementioned problems of evaporative scent burner, this industry shall assume the responsibility to make pioneering R&D and innovation for an ideal utility model of evaporative scent burner.

BRIEF SUMMARY OF THE INVENTION

Based upon the structure and composition as above specified, it is understood that the volatile evaporative scent burner in the present invention, which differs from either igniting or electric evaporative scent burner, requires no ignition or electricity. So, it is not prone to explosion, thereby offering an improved safety and lower cost. As shown in FIG. 3 for the evaporation path of the essential oil, firstly, the braided wire 30 will absorb the essential oil W contained in the bottle 10 until braided wire head 31, then the essential oil W will cross the capillary porosity of the gypsum evaporative base 20 for evaporation. Thereupon, available with the feature of capillary porosity for polymeric gypsum, the gypsum evaporative base 20 can be applied for evaporation of essential oil. Also, based upon the structural design that the top of gypsum evaporative base 20 is designed with an enlargement surface 21, a desirable evaporation effect of essential oil is possible due to its enlarged evaporation area and higher speed.

The present invention has modified the design of reinforcement base 40 for an improved efficiency. Thus, the ring-type wall 42 can separate the braided wire 30 from gypsum evaporative base 20, and prevent the gypsum evaporative base 20 from breakdown or strip during assembly and packaging or utilization, thus providing the customers with a leak-proof product.

DETAILED DESCRIPTION OF THE INVENTION

The features and the advantages of the present invention will be more readily understood upon a thoughtful deliberation of the following detailed description of a preferred embodiment of the present invention with reference to the accompanying drawings.

Figure 1:
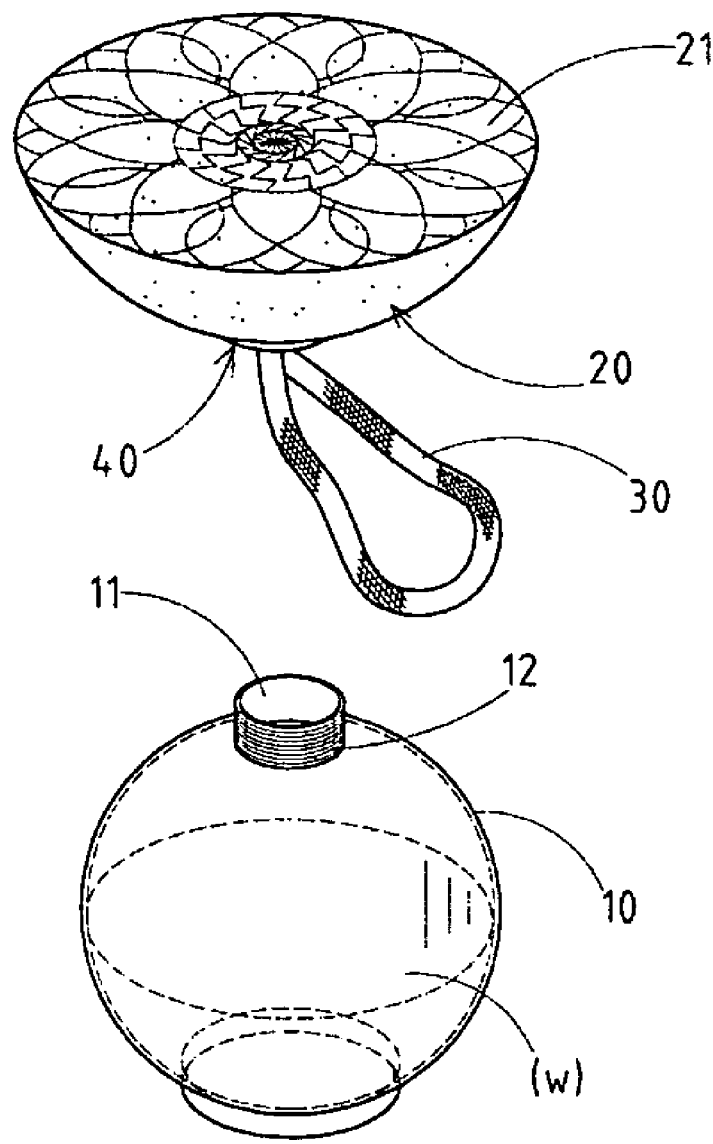
FIG. 1 shows an exploded perspective view of the present invention.
Figure 2:
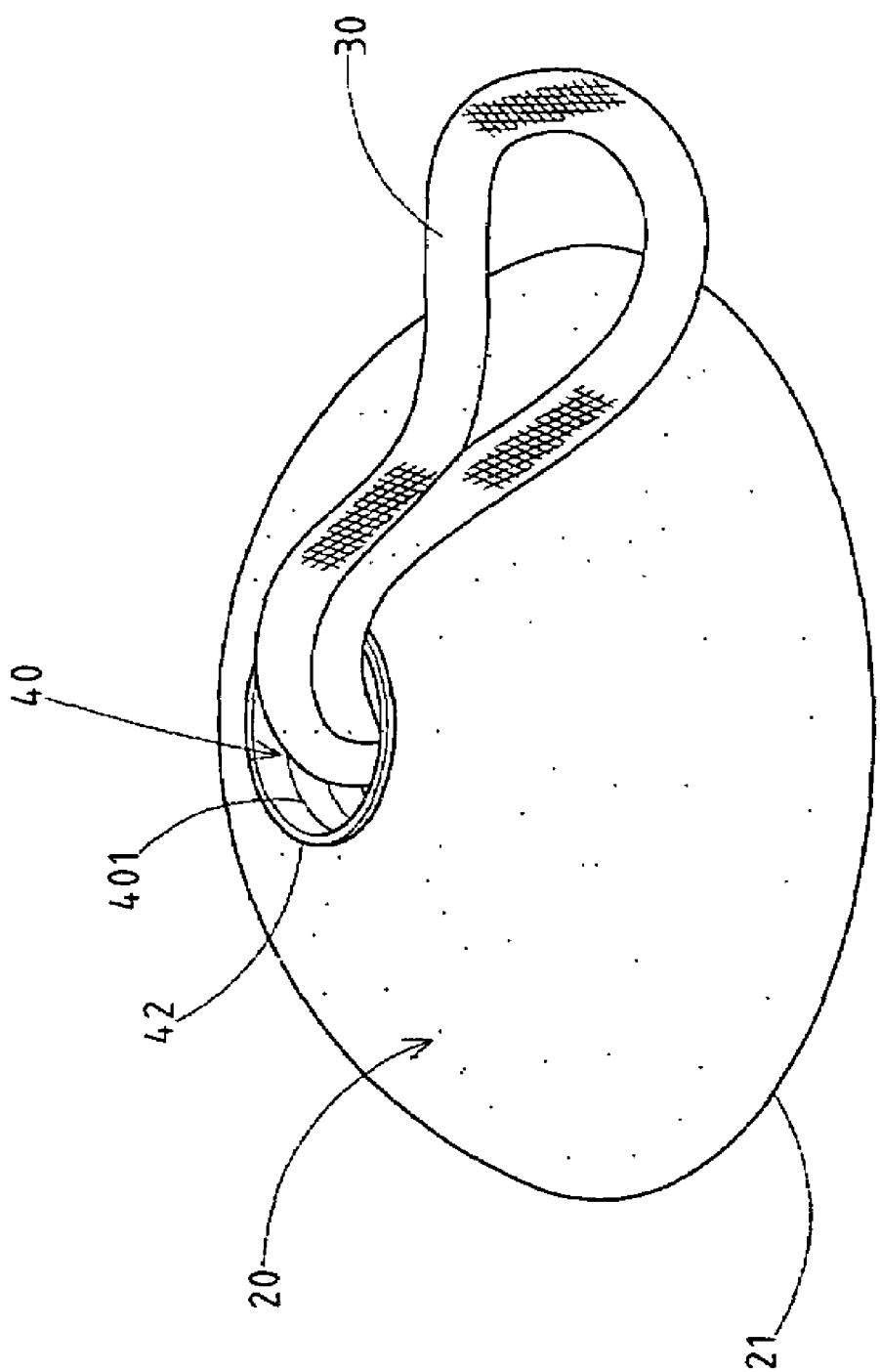
FIG. 2 shows a perspective view of the gypsum evaporative base.
Figure 3:
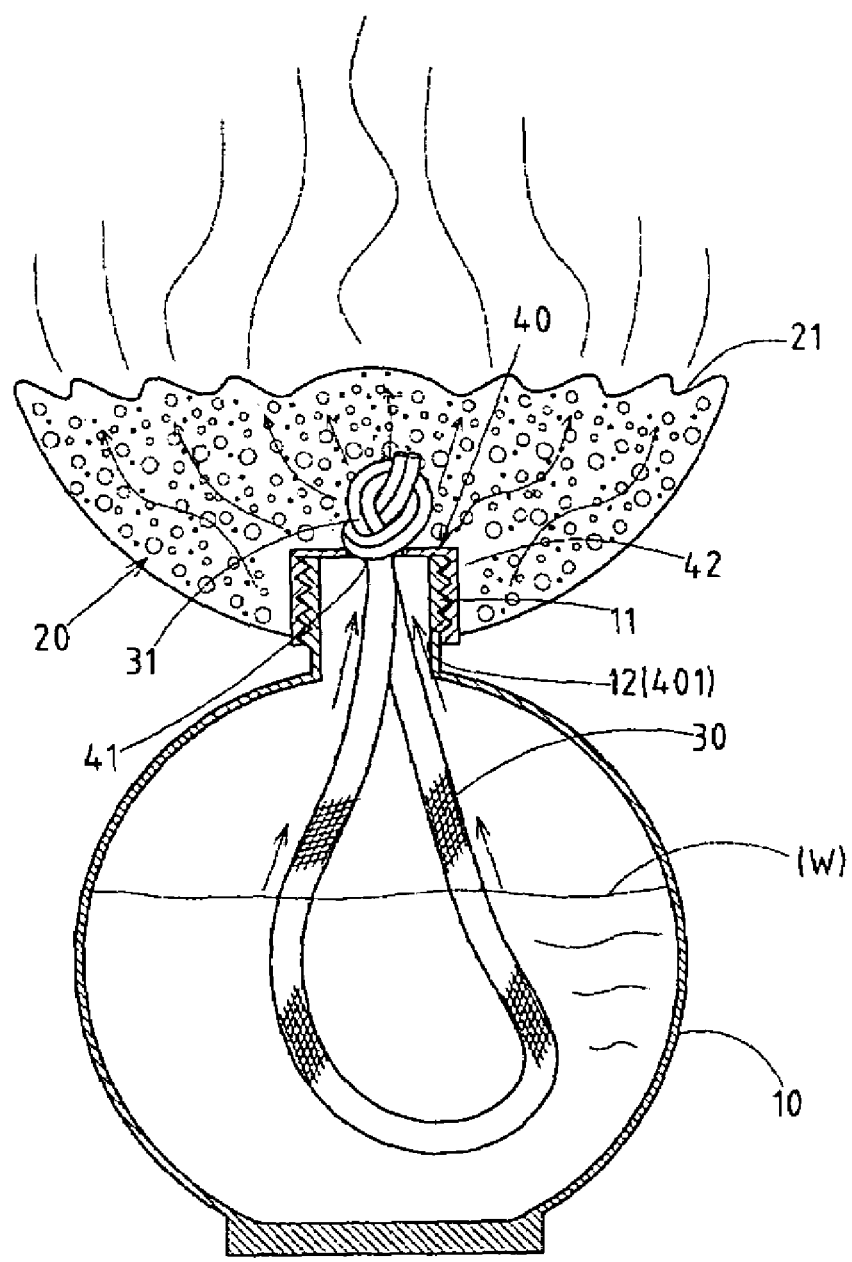
FIG. 3 shows a cross-sectional view of the assembly of the present invention.

As shown in FIGS. 1–3, there is an evaporative scent burner embodied in the present invention.

The present invention includes a bottle 10 of optional sizes, which is used to accommodate the essential oil W (as shown in FIG. 3), with its top provided with a bottle mouth 11. And, a screw thread 12 is mounted at the periphery of the bottle mouth.

The invention also has a gypsum evaporative base 20, which bottom is provided onto the bottle mouth 11 of above-mentioned bottle 10 while its top can be designed with an enlargement surface 21 for a larger area of evaporation, e.g. a flower shape (as shown in FIGS. 1 and 3).

The present invention further includes a braided wire 30, which is connected to the gypsum evaporative base 20 while the bottom of the braided wire 30 will fall inside the bottle 50 to absorb essential oil 55.

There is also a reinforcement base 40, which is built-in the gypsum evaporative base 20. Constructed of rigid materials of strong toughness (e.g. plastics, metals and timbers), the reinforcement base 40 is provided with a screw notch 401 where a screw thread 12 at the periphery of bottle mouth 11 can be properly screwed. And, a punching hole 41 is provided inside the screw notch 401, where a braided wire 30 can cross through and the braided wire head 31 can be fastened. Besides, this reinforcement base 40 is available with a ring-type wall 42 to separate braided wire 30 and gypsum evaporative base 20, with its aim of preventing the gypsum evaporative base 20 from breakdown or strip or leakage.

Figure 4:
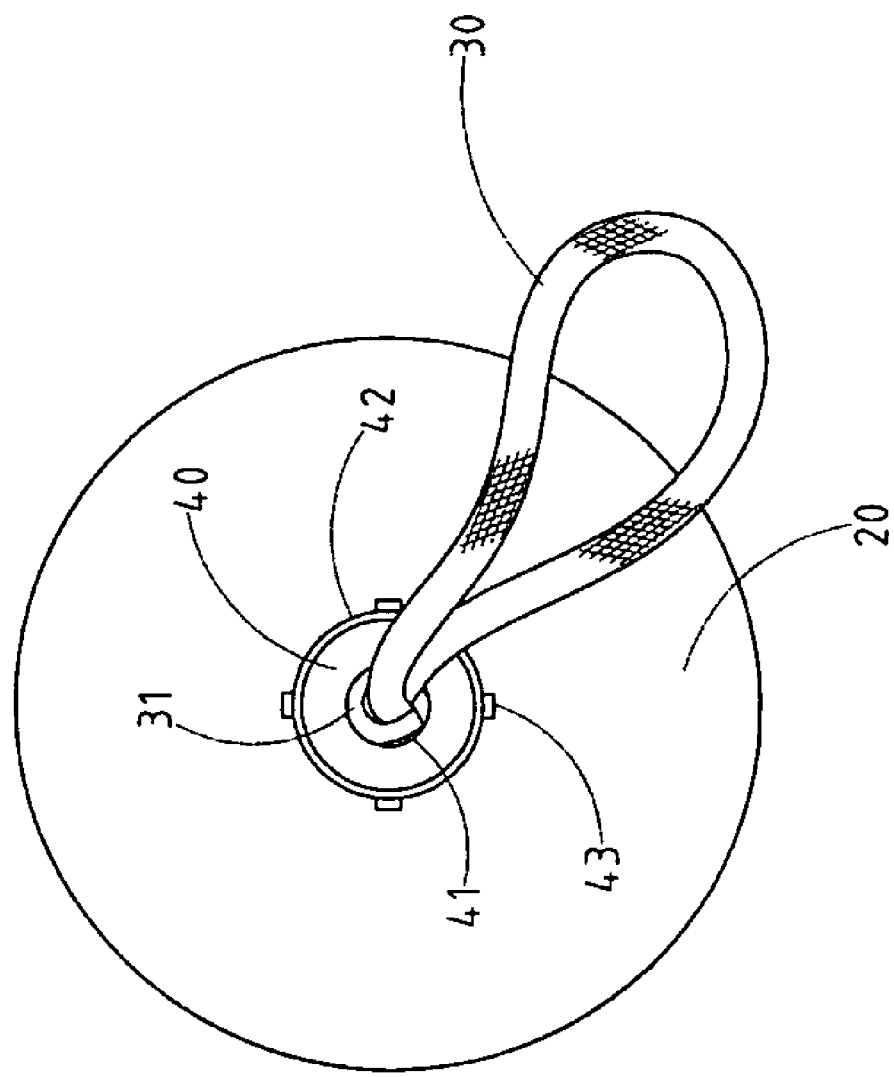
FIG. 4 shows a top plan view of the present invention.
Figure 5:
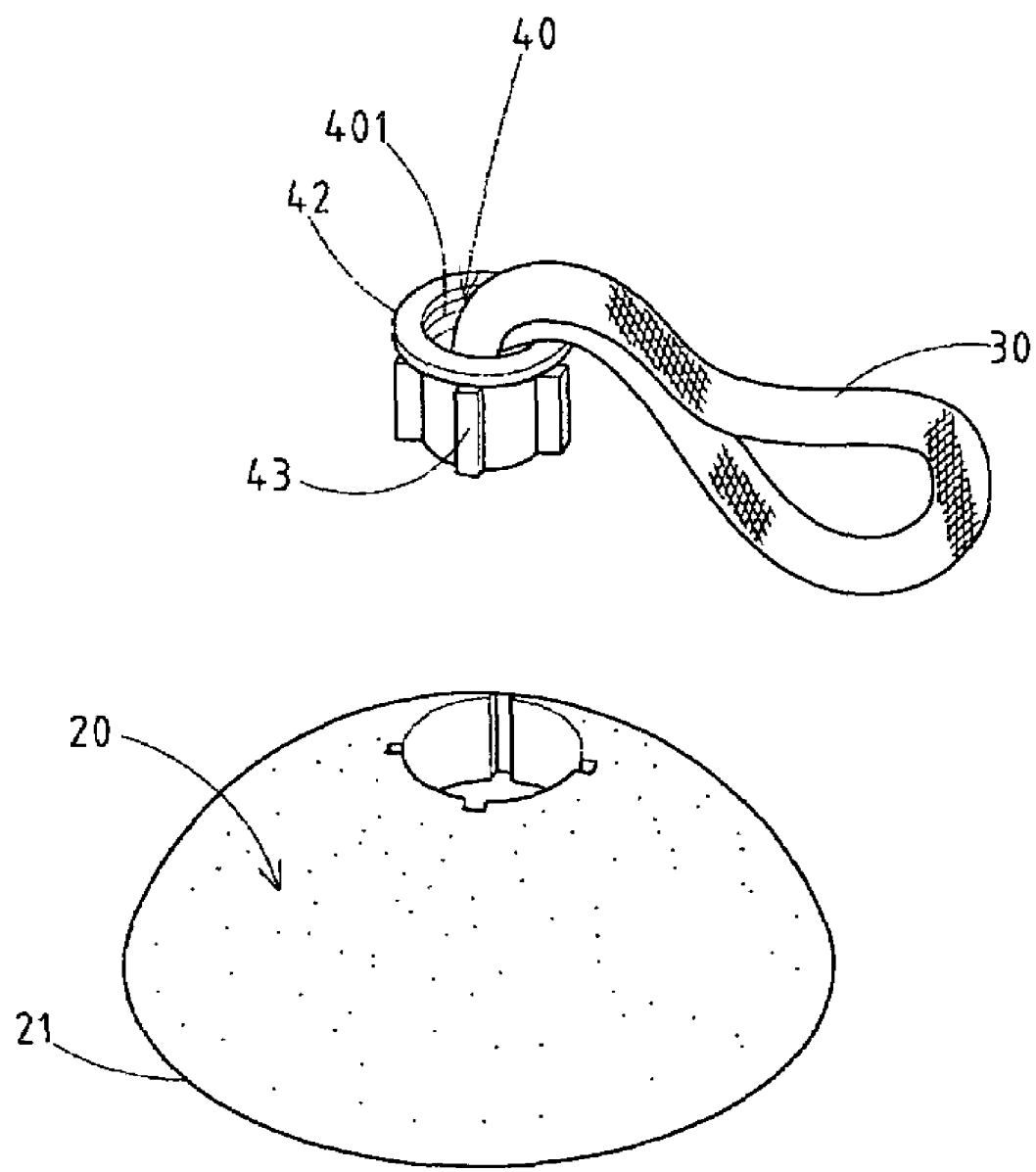
FIG. 5 shows an exploded perspective view of the reinforcement base.
Figure 6:
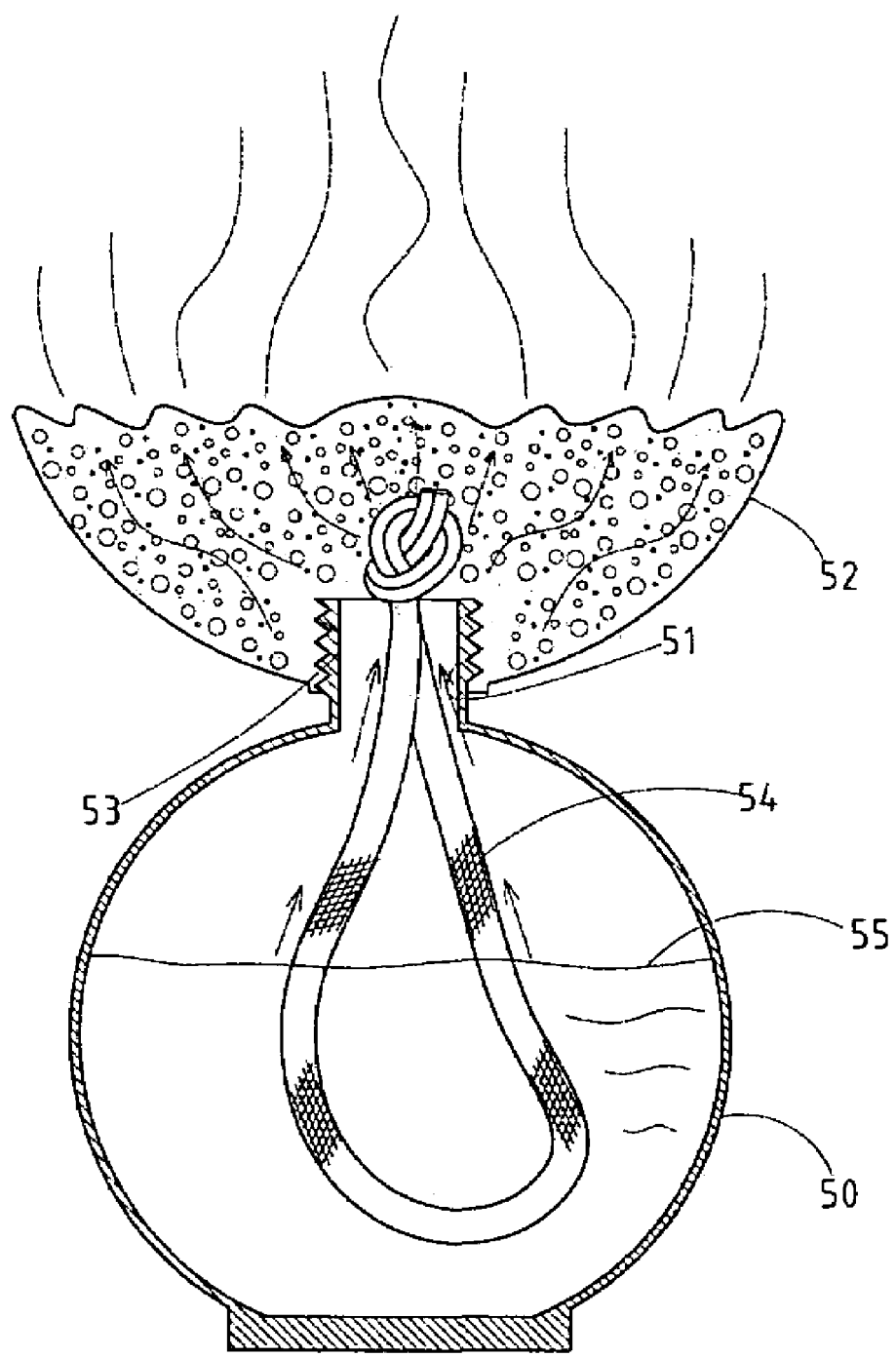
FIG. 6 shows a cross-sectional view of the assembly of the present invention.
Figure 7:
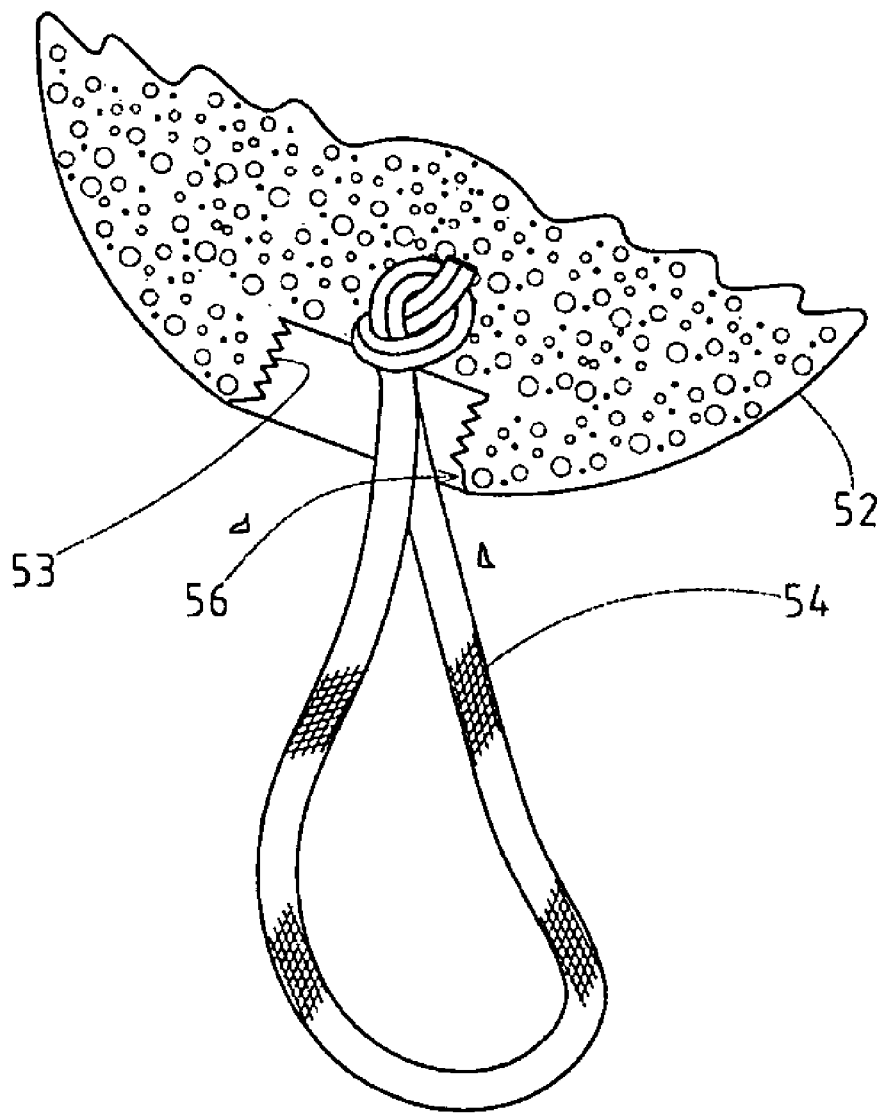
FIG. 7 shows a schematic view of the fragile helical tooth of the screw hole.

As shown in FIGS. 4 and 5, convex rib 43 can be separately mounted at the outer flank of the ring-type wall 42 of reinforcement base 40, thereby fastening securely the gypsum evaporative base 20.

As shown in FIG. 3, the bottom of ring-type wall 42 of the reinforcement base 40 can protrude from the gypsum evaporative base 20. So, when the gypsum evaporative base 20 is installed onto the bottle mouth 11, the bottom of the ring-type wall 42 of reinforcement base 40 can insert the inner wall of the bottle mouth 11 for a desirable fixation.

I claim:

1. An evaporative scent burner comprising:
   a bottle used to accommodate essential oil, having a top provided with a bottle mouth and a screw thread mounted at a periphery of the bottle mouth;
   a gypsum evaporative base, having a bottom provided onto the bottle mouth of said bottle while a top thereof has an enlargement surface for a larger area of evaporation;
   a braided wire with a head connected to the gypsum evaporative base while the bottom of the braided wire will fall inside the bottle to absorb essential oil wherein a reinforcement base is built-in in the gypsum evaporative base and comprised of rigid materials of strong toughness, the reinforcement base being provided with a screw notch where a screw thread at the periphery of bottle mouth can be properly screwed and a punching hole is provided inside the screw notch, where a braided wire can cross through and the braided wire head can be fastened, wherein said reinforcement base is available with a ring-type wall to separate braided wire and gypsum evaporative base, with its aim of preventing the gypsum evaporative base from breakdown or strip or leakage.

2. The evaporative scent burner defined in claim 1, wherein a convex rib can be separately mounted at the outer flank of the ring-type wall of reinforcement base, thereby fastening securely the gypsum evaporative base.

3. The evaporative scent burner defined in claim 1, wherein said bottom of ring-type wall of the reinforcement base can protrude from the gypsum evaporative base wherein, when the gypsum evaporative base is installed onto the bottle mouth, the bottom of the ring-type wall of reinforcement base can be inserted into the inner wall of the bottle mouth for a desirable fixation.

\* \* \* \* \*